United States Patent [19]

Terasaki et al.

[11] Patent Number: 4,599,315
[45] Date of Patent: Jul. 8, 1986

[54] MICRODROPLET TEST APPARATUS

[75] Inventors: Paul I. Terasaki; Dennis Aoki, both of Los Angeles, Calif.

[73] Assignee: University of California Regents, Berkeley, Calif.

[21] Appl. No.: 531,923

[22] Filed: Sep. 13, 1983

[51] Int. Cl.[4] .......... C12Q 1/20; C12M 1/26; C12M 1/32; C12M 1/28

[52] U.S. Cl. .......... 435/301; 435/33; 435/292; 435/294; 435/298; 435/299; 435/300; 435/293; 435/810; 436/180; 436/809; 422/73; 422/99; 422/102; 350/536; 356/244; 356/246

[58] Field of Search .......... 435/33, 293, 300, 292, 435/294, 298, 299, 301, 810; 436/809, 180; 422/102, 73, 99; 356/246, 244; 350/536

[56] References Cited

U.S. PATENT DOCUMENTS

| | | | |
|---|---|---|---|
| 2,956,931 | 10/1960 | Goldberg | 435/293 |
| 3,912,596 | 10/1975 | Haque et al. | 435/294 |
| 4,057,470 | 11/1977 | Schrof | 435/298 |
| 4,278,437 | 7/1981 | Haggar | 422/73 |
| 4,294,924 | 10/1981 | Pepicelli et al. | 435/299 |
| 4,324,859 | 4/1982 | Saxholm | 435/7 |
| 4,358,908 | 11/1982 | Song | 435/287 |
| 4,432,642 | 2/1984 | Tolles | 356/338 |
| 4,483,925 | 11/1984 | Noack | 436/809 |

OTHER PUBLICATIONS

Terasaki et al., Microdroplet Testing for HLA-A, -B, -C and -D, Antigens, Am. Journal of Clin. Path., vol. 69, No. 2, Feb. 78.

Primary Examiner—Robert J. Warden
Assistant Examiner—L. Krawczewicz
Attorney, Agent, or Firm—Poms, Smith, Lande & Rose

[57] ABSTRACT

A microdroplet test apparatus for use in HLA typing. The apparatus is an improvement upon the well known Terasaki tray which is in use for determining HLA antigens by measuring lymphocyte cytotoxicity. The apparatus includes a tray having a plurality of microtest wells wherein the sides of the microtest wells are designed to promote localization of lymphocytes or other cells being tested at the microtest well bottom. The apparatus further includes a cover having either rods or tubes which extend down into the test solution present in the microtest well to thereby control the amount of test solution which is present in the cylindrical optical view path through which the test solution is viewed by microscope for test result measurements. This allows control of the amount of test solution in the optical view path in order to reduce the amount of solution which must be looked through when cells are being counted or alternatively, increasing the amount of test solution present in the view path in order to maximize detection when a colored reaction product in the test solution is being measured.

4 Claims, 6 Drawing Figures

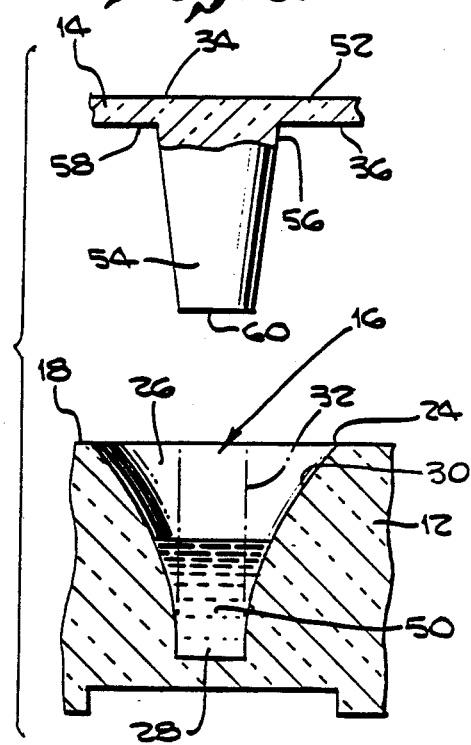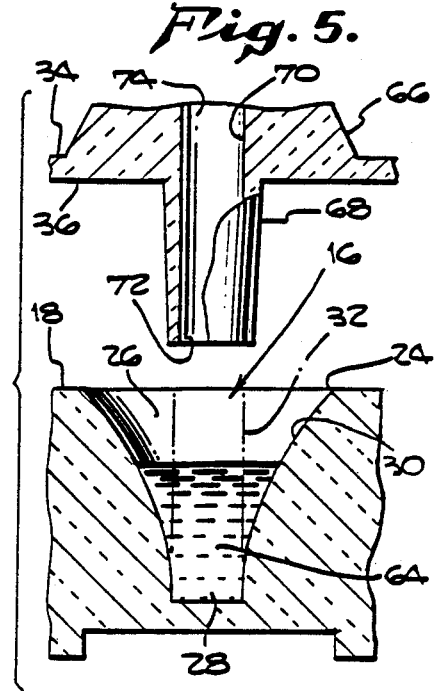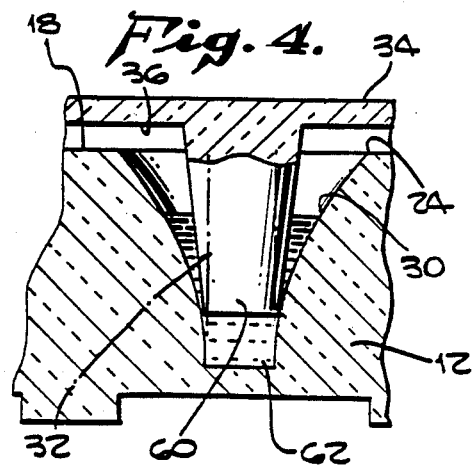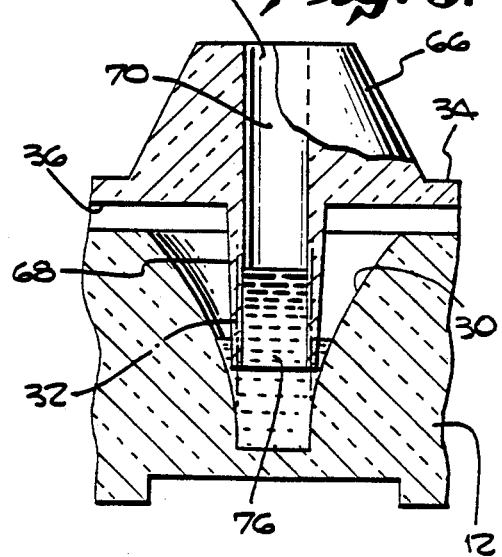

MICRODROPLET TEST APPARATUS

BACKGROUND OF THE INVENTION

The present invention relates generally to an improved microdroplet test apparatus used in determining human leukocyte antigens (HLA antigens) by measuring lymphocyte cytotoxicity. More specifically, the present invention relates to an improved microdroplet test tray design and improved tray cover structures which are designed to enhance the accuracy and usefulness of the microdroplet test system.

The microdroplet lymphocyte cytotoxicity test was introduced in 1964 by Terasaki, P. I., McClelland, J. D.: Microdroplet Assay of Human Serum Cytotoxins. Nature 204: 998–1000, 1964. Since that time, the microdroplet lymphocyte cytotoxicity test has gained universal acceptance as the method of choice to test for HLA antigens.

The basic microlymphocyte cytotoxicity test consists of reacting 0.001 milliliters of lymphocytes with 0.001 milliliters of a specific antibody which is known to be reactive with a specific HLA antigen. If the lymphocytes contain the specific antigen being tested for, the antibodies will bind to the lymphocytes. Measurement of the degree of binding between the specific antibody and the lymphocytes is accomplished by adding 0.005 milliliters of rabbit complement into the test well containing the lymphocytes and antibody. The rabbit complement promotes lysing of those lymphocytes which have reacted with the antibody. Measurement of the antibody-lymphocyte reaction is then measured by viewing the test solution in the test cell with a 10× microscope to determine the degree of lymphocyte lysis.

In order to provide a suitable means for handling these minute quantities of reagents and additionally to provide an apparatus in which numerous tests can be carried out simultaneously, a plastic tray with multiple microtest wells was developed. These trays, which are commonly known as "Terasaki Trays" are widely known and used for microdroplet testing of HLA antigens. The microtest wells in the Terasaki tray are circular frusto-conical wells having an inwardly sloping funnel-shaped straight side wall of constant slope. The inwardly sloping side wall terminates at the microtest well bottom. The microtest well bottom has a circular cross section which is designed to be equal to the area which is visible in the single field of a 10× microscope objective when the test wells are viewed from directly above and adjacent to the tray. This allows the technician to view the entire test reaction (i.e. cell lysis) in one field of the microscope.

Although the Terasaki tray has experienced wide popularity and is well suited for its intended purpose, some difficulty has been experienced with lymphocytes sticking or not flowing completely down the constant slope microtest well side wall. It is critical that the entire sample of lymphocytes to be tested be placed at the bottom of the microtest well. If the lymphocytes become stuck or otherwise adhere to the upper portions of the microtest cell side wall, a false positive test result is possible. It therefore would be desirable to provide an improved tray in which the test wells are shaped to prevent retention of lymphocytes on the microtest cell side walls to thereby promote localization of the lymphocytes at or near the microtest well bottom.

During HLA testing, one or more reagents which are themselves colored or which produce a colored product may be utilized. Further, certain test solutions may be opaque. These colored test solutions make it difficult to count the number of lysed leukocytes remaining at the bottom of the microtest well after completion of the test. It would be desirable to provide an apparatus in which the amount of colored solution through which the technician must look to view the leukocytes can be reduced.

The microtest tray can also be used for various testing procedures in which a colored product is produced. In these situations, it is many times desirable to increase the depth of test solution in the microtest well without increasing the total amount of reagents and cells utilized in order to increase the detection limits of the procedure. It would be desirable to provide some type of apparatus which could be combined with the Terasaki Tray to provide this desired increase in optical path through the test solution in order to maximize color intensity for measurement.

SUMMARY OF THE INVENTION

In accordance with the present invention, a microdroplet test apparatus is disclosed for use in determining HLA antigens by measuring lymphocyte cytotoxicity. The present apparatus basically includes a microdroplet testing tray having a plurality of microtest wells at spaced locations. The microtest wells are designed to receive test solutions which typically will include lymphocytes and selective cytotoxic reagents such as antibodies and complement. The microtest wells include an upper rim located on the tray top which defines an opening in the tray which is of a sufficient surface area to allow convenient introduction of small quantities of lymphocytes and reagents into the microtest wells. The microtest wells further include a bottom having a surface area less than the surface area of the well opening and a well side wall extending between the upper rim and the well bottom. The microtest well includes a central cylindrical zone extending vertically upward from the well bottom and defining a vertical view path wherein lymphocyte cytotoxicity or any other test result is visually measured by viewing vertically down through the test solution in the vertical view path.

As a particular feature of the present invention, the side wall of the microtest wells has a vertical cross section which is arcuate. The slope of the arcuate side wall is less than vertical adjacent the microtest well rim and increases to a substantially vertical slope adjacent the well bottom. The arcuate shape and continuously increasing vertical slope of the microtest well wall promotes localization of the lymphocytes toward the well bottom to insure complete reaction of lymphocytes and antibodies in the test well.

As an additional feature of the microdroplet test apparatus, a tray cover is provided which has a top surface, bottom surface and a perimeter. Means are associated with the perimeter of the tray cover for providing a seal between the tray cover and the microtest tray to thereby prevent evaporation of the test solution. Further, the cover tray is provided with view path control means located on the cover which extend downward from the cover bottom and are insertable within the microtest well for controlling the amount of test solution present in the vertical view path. This thereby provides selective control of the depth of solution in the vertical view path through which the technician must look when taking visual measurements.

As one particular feature of the present invention, the view path control means is provided by a solid rod of optically clear plastic or glass which is integral with and extends downward from the cover plate in the view path and into the test solution. The solid rod displaces test solution from the optical view path thereby reducing the depth of solution which must be viewed through. By viewing down through the optically clear rod, the technician can now clearly view cells or other desired items present on the microtest well bottom even though the solution may be colored or turbid.

As another feature of the present invention, the view path control means may be provided by a tube which extends through the tray cover and down into the test solution. The tube is positioned so that the internal conduit of the tube is coaxial with the vertical view path. The internal conduit and tube are appropriately sized so that a portion of the test solution is drawn up into the conduit by capillary action to thereby increase the depth of test solution present in the view path. This feature is useful when the reaction product or test result involves the development of a color which must be measured either visually or by suitable photo detectors since it increases the color intensity in the view path and thereby increases the accuracy of the measurement and allows detection of smaller quantities.

The above-discussed and many other features and attendant advantages of the present invention will become apparent as the invention becomes better understood by reference to the following detailed description when considered in conjunction with the accompanying drawing.

BRIEF DESCRIPTION OF THE DRAWINGS

FIG. 3 is a detailed sectional view showing an exemplary embodiment of the present invention in which the cover plate and tray are designed to reduce the amount of test solution present in the optical view path. The cover and tray are shown in their disengaged positions.

FIG. 4 is same as FIG. 3 except that the cover has been placed in its sealing position upon the microtest tray.

FIG. 5 is a detailed sectional view of another exemplary embodiment of the present invention in which the cover and test tray are designed to increase the depth of solution present in the optical view path. The cover is shown positioned over the tray but displaced therefrom.

FIG. 6 is a same as FIG. 5 except that the cover is shown in its sealing position upon the microtest tray.

DETAILED DESCRIPTION OF THE INVENTION

Figure 1:
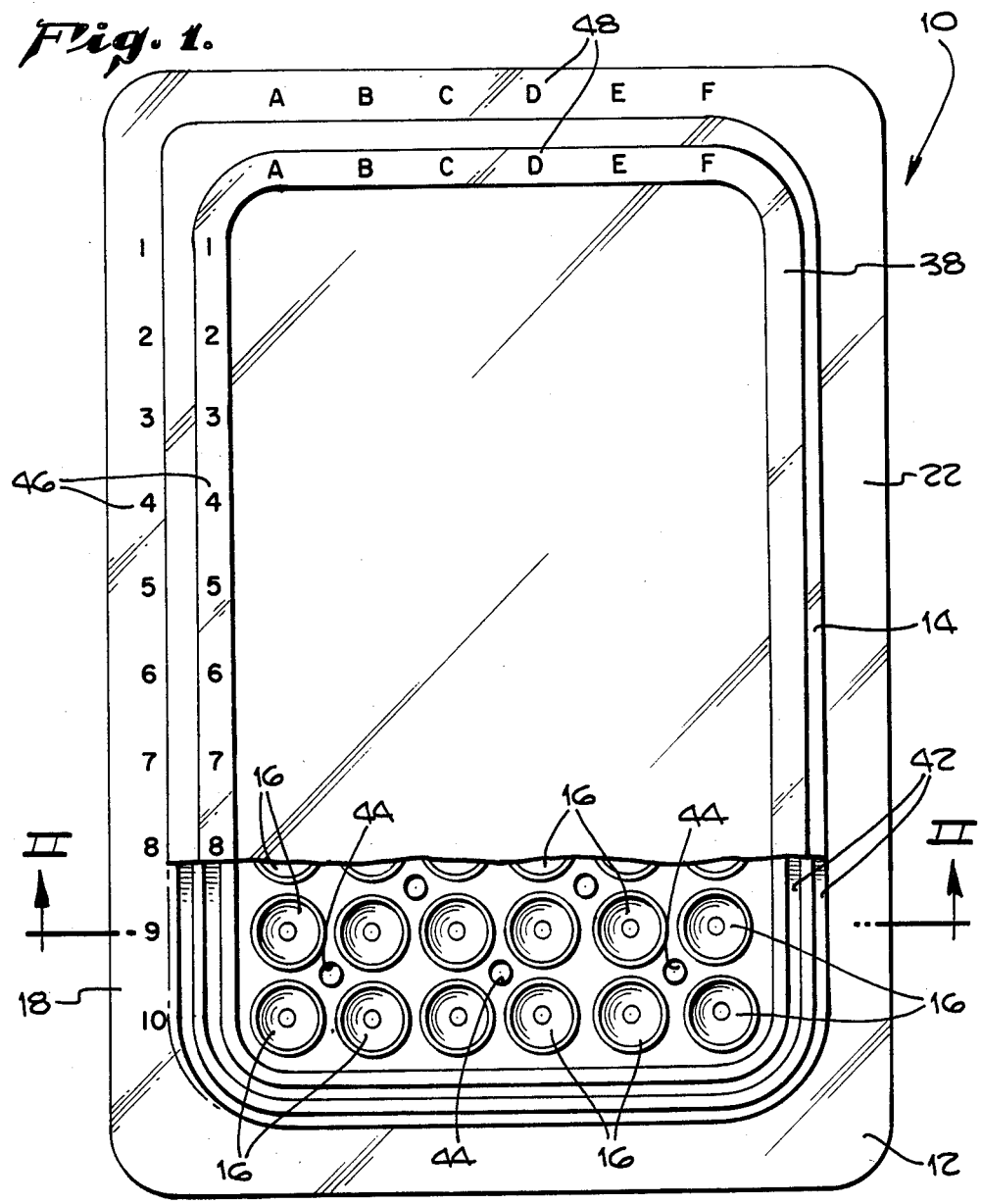
FIG. 1 is a top view of an exemplary preferred microdroplet test apparatus in accordance with the present invention.
Figure 2:
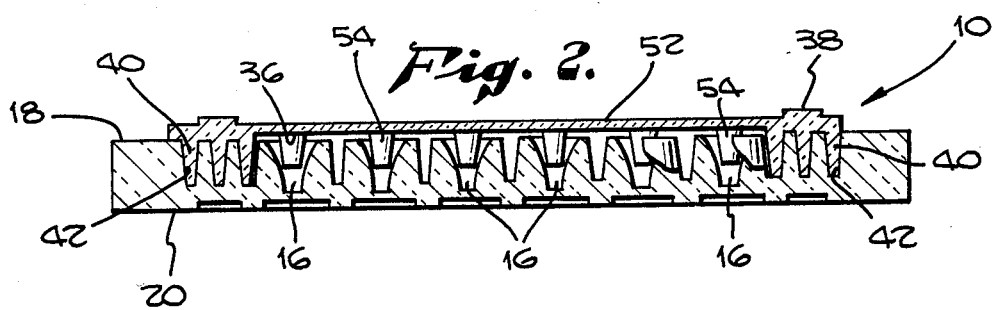
FIG. 2 is a sectional view of FIG. 1 taken in the II—II plane.

The improved microdroplet test apparatus in accordance with the present invention is shown generally at 10 in FIGS. 1 and 2. The test apparatus 10 includes a tray 12 and a cover or coverplate 14. The tray 12 is preferably made from plastic or other relatively inert material and includes a plurality of microtest wells 16 which may be molded, machined or otherwise formed in the tray 12. The tray 12 also includes a top surface 18, a bottom surface 20 and a perimeter 22.

As best shown in FIGS. 3-6, the microtest wells 16 include an upper rim 24 on the tray top surface 18 which defines an opening 26 which is of a sufficient surface area to allow introduction of lymphocytes or other types of cells and reagents into the microtest well 16. The microtest well 16 further includes a bottom 28 and a well side wall 30 extending between the upper rim 24 and the well bottom 28. The microtest well 16 includes a central cylindrical zone shown in phantom at 32 which defines a vertical view path wherein lymphocyte cytotoxicity or other measurable characteristics are measured by viewing vertically down through the test solution present in the vertical view path 32.

The well side wall 30 has an arcuate cross section, as best shown in FIGS. 3-6, wherein the slope of the side wall 30 gradually increases from less than vertical near the well rim 24 to substantially vertical at the well bottom. This is an improvement over the prior Terasaki trays where the side wall has a constant slope, since the increasing slope of side wall 30 promotes localization of the lymphocytes at the well bottom 28.

The cover 14 includes a top surface 34, a bottom 36 and a perimeter 38. Tongues or ridges 40 are provided (as best shown in FIG. 2) which extend around the cover perimeter 38 for making engagement with grooves 42 in the tray 12. The tongue and groove arrangement around the perimeters of the cover 14 and tray 12 provides means for sealing the cover 14 to tray 12. Other means for sealing the perimeters of the cover 14 to tray 12 may be utilized including various sealant materials, such as wax, polymer sealants or any other sealing system in which an air tight seal between the cover 14 and tray 12 is provided.

The tongues 40 and grooves 42 provide a sealing arrangement which also provides for precise positioning of the cover 14 in relation to tray 12. In addition to the tongues 40 and grooves 42, pegs may be included on cover 14 (not shown) for insertion into holes 44 present in the tray 12 to provide additional accurate positioning of the cover 14 on the tray 12.

As best shown in FIG. 1, it is preferred that both the tray 12 and cover 14 be provided with alpha and/or numeric indicia shown generally at 46 and 48. The indicia is provided to allow specific identification of each microtest well 16.

Referring now to FIGS. 3 and 4, the tray 12 is shown containing a test solution 50. The test tray 12 is designed specifically for testing HLA antigens and therefore the test solution will generally include leukocytes (usually lymphocytes) and various specific antibodies and complement. Many times, the test solution 50 will be colored or may be turbid or opaque. In these situations, it is preferable to reduce the amount of test solution which is present in the verical view path 32. In accordance with the present invention, cover 52 is provided with a plurality of view path control means, such as solid rods 54 which are made from an optically clear material such as clear plastic or glass. The rod 54 includes a base 56 which is attached to the cover bottom 58 by any convenient means. Preferably, the cover 52 and rod 54 are molded simultaneously together to form an integral cover. As shown in FIG. 4, when the cover 52 is positioned onto tray 12, the tip 60 of rod 54 extends into the test solution 50 so as to displace test solution from the view path 32 to thereby reduce the depth of test solution in the view path as shown at 62. The cross-sectional area and length of rod 54 may be varied depending upon the amount of test solution 50 which is desired to be diplaced from the vertical view path 32. For particularly turbid colored test solutions, longer rods may be preferred in order to remove as much test solution from the vertical view path 32 as possible while still leaving the lymphocytes or other cells at the microtest well bottom 28 for viewing. Preferably the rod 54 is tapered as shown so that the base 56 has a greater cross-sectional area than the tip 60.

In other microtest procedures, test measurements or detections are based on the detection or measurement of the amount of color or other visual indicator present in the test solution. In these situations, it is desirable to maximize the amount of test solution present in the optical view path 32 as much as possible. As shown in FIG. 5, a test solution 64 is present within microtest well 16. In accordance with the present invention, a cover 66 is provided which includes a view path control means, such as tube 68 which is attached to the cover and positioned to extend vertically downward into the microtest well 16 when the cover is placed in position on the tray 12 as shown in FIG. 6. The tube 68 includes an internal conduit 70 which has an open bottom end 72 and open top end 74. As shown in FIG. 6, the test solution 64 is drawn up into the internal conduit 70 by capillary action to thereby effectively increase the depth of test solution 64 present in the view path 32 as shown at 76. For most cases, the amount of test solution pulled up into conduit 70 by capillary action will be sufficient to increase the amount of test solution in the view path 32 to desired levels. When it is desired to increase the amount of test solution in the optical view path 32 further, various apparatus such as vacuum systems or other conventional apparatus for creating negative pressure may be connected to conduit 70 in order to increase the amount of solution drawn into conduit 70. As can be seen from FIGS. 3–6, the present invention provides a particularly useful and simple means for controlling the amount of test solution which is present in the microtest well veiw path 32.

The overall size of tray 12 and cover 14 are typically around 2 inches by 3 inches. The microtest wells are arranged in an array which preferably includes about 60 microtest wells 16. The overall area covered by the microtest well array is preferably around 1½ inch by 2½ inches. Each microtest well is preferably approximately 3/16 inch in diameter at the upper rim 24 with the microtest well bottom 28 having a circular surface area which is equivalent to the field of view seen through a 10 power microscope when the microscrope lens is placed adjacent the cover for viewing down through the vertical view path 32.

Although the microdroplet testing tray 12 and cover 14 may be used in a wide variety of microtest procedures, it is particularly well suited for use in the microdroplet testing for HLA antigens. The following is exemplary of a preferred use for the microdroplet test apparatus in accordance with the present invention.

0.001-ml of the desired specific antisera is put into the tray wells 16 with a serum dotting machine. This is followed by the addition of 0.005-ml of mineral oil. This sequence permits the dispensing of antisera into the center of the well. Without a machine it is necessary to reverse the sequence, that is, oil is added to the trays first and the antisera second, because the sera would evaporate before oil could be added. Manual adding of sera to the trays containing oil must be done carefully since the droplets tend to float on oil and stick to the sides of the test wells. To check proper placement, the sera are stained with phenol red to aid in visual observation. All these procedures are carried out on a table with built-in fluorescent lights beneath the table surface. It is important to examine the trays with this type of lighting to insure that all dots are in place. When a serum is missing it should be either added by hand or the well cancelled out by marking the bottom of the trays with a marking pen, since the absence of the serum in a given well will not be known once the tray is stained and fixed.

After preparation, the trays are stored at $-70°$ C. Storage for more than several months often results in the formation of bubbles. Trays should not be stored in a $CO_2$ atmosphere on dry ice since the acidity tends to destroy the activity of sera. When shipped in dry ice, trays are enclosed in either a tightly sealed glass container or an aluminum sealed container.

It is important that all sera be centrifuged at high speeds to eliminate debris and lipids that come to the top of the tube. Sera are clarified either by ultracentrifugation at 35,000 rpm for 40 min. or by centrifugation of Beckman tubes at 15,000 rpm for 15 min. with the Beckman microfuge placed inside a refrigerator. The advantage of the Beckman tubes is that the lipids that rise to the top can be cut off with a razor blade. With ultracentrifugation, the serum is withdrawn from below by piercing the cellulose tube with a syringe and needle. This step is important to assure that the sera within the wells are as clean as possible. The presence of debris tends to make reading difficult and increases reading errors. As previously described, the use of the tray cover shown in FIGS. 3 and 4 reduces this problem.

Lymphocytes are added to the typing trays in 0.001-ml volume with the use of a 0.05-ml syringe attached to a repeating dispenser. The dotting of the trays requires careful addition of the lymphocytes and mixing of the microdroplets within wells. The arcuate sides of the wells 16 makes this step easier by promoting localization of the cells near the well bottom. An electrostatic mixer or a wire is used to insure that the wells are mixed. Trays are incubated in a controlled temperature incubator at 25° C.

Following ½ hour incubation, 0.005-ml of complement is added. After a further 1-hr incubation at 25° C., 0.005-ml of eosin dye is added, followed 2 min. later by 0.005 ml of formaldehyde. The trays are then covered with cover 52. Prevention of evaporation of the reagents as well as containment of formaldehyde is accomplished by the tongue and groove seal 40 and 42. Formation of bubbles in the tray can be reduced by storing trays in the refrigerator. Trays can be read with a 10 power microscope over a 1 to 2 week period after sealing by counting the number of unlysed cells present on the microtest well bottom.

Having thus described exemplary embodiments of the present invention, it should be noted by those skilled in the art that the disclosures within are exemplary only and that various other alternatives adaptations and modifications may be made within the scope of the present invention. Accordingly, the present invention is not limited to the specific embodiment as illustrated herein and is only limited in accordance with the following claims.

What is claimed is:

1. A microdroplet test apparatus adapted for use in determining HLA antigens by measuring lymphocyte cytotoxicity, said apparatus comprising:

a tray having a top surface, a bottom surface and a perimeter;

a plurality of microtest wells at spaced locations in said tray for receiving and holding test solutions including lymphocytes and selective cytotoxic reagents capable of lysing selected lymphocytes, said microtest wells including an upper rim on said tray top surface defining an opening in said tray top surface having a surface area sufficient to allow introduction of lymphocytes and reagents into said wells, a bottom having a surface area less than the surface area of said well opening and a well side wall extending between said upper rim and said well bottom, said microtest well including a central cylindrical zone defining a vertical view path wherein lymphocyte cytotoxicity is measured by determining the degree of lymphocyte lysis by viewing vertically down through the test solution present in said vertical view path and wherein said well side wall has a circular rim and the vertical cross section of said wall is arcuate, such that the slope of said side wall is less than vertical adjacent said circular rim and increases to substantially vertical slope adjacent said well bottom to thereby promote localization of said lymphocytes toward said well bottom;

a cover for said tray having a top surface, a bottom surface and a perimeter;

means associted with the perimeters of said tray and said cover for providing a seal therebetween when said cover is placed on said tray;

view path control means located on said cover extending downward from said cover bottom and insertable within said microtest wells for controlling the amount of test solution present in said vertical view path, wherein said view path control means includes a tube attached to said cover and positioned to extend vertically downward into said microtest well when said cover is in position on said tray, said tube having an internal conduit along said view path with an open bottom end which is insertable into said test solution wherein said tube and internal conduit are sized such that said test solution is drawn up into said conduit by way of capillary action to provide an increase in the depth of said test solution in said view path.

2. A microdroplet test apparatus according to claim 1 wherein said means for sealing said cover to said tray is provided by one or more mating tongue and groove surfaces extending around the perimeter of said cover and said tray.

3. A cover for a microdroplet test tray wherein said test tray includes a top surface, a bottom surface, a perimeter and a plurality of microtest wells at spaced locations in said tray for receiving and holding test solutions including lymphocytes and selective cytotoxic reagents capable of lysing selected lymphocytes, said microtest wells including a central vertical cylindrical zone defining a vertical view path, said cover comprising:

a cover plate having a top surface, a bottom surface and perimeter for sealing engagement with the perimeter of said tray;

means associated with said cover plate perimeter for sealing said cover plate to said tray when said cover plate is positioned on said cover plate; and view path control means located on said cover plate extending downward from said cover plate bottom and insertable within said microtest wells for controlling the amount of test solution present in said vertical view path to thereby provide selective control of the depth of solution in said vertical view path, said view path control means including a tube attached to said cover plate and positioned to extend vertically downward into said microtest well when said cover plate is in position on said tray, said tube having an internal conduit along said view path with an open bottom end which is insertable into said test solution wherein said tube and internal conduit are sized such that said test solution is drawn up into said conduit by way of capillary action to provide said increase in the depth of said test solutions in said view path.

4. In a microtest tray having a top surface, a bottom surface, a perimeter and a plurality of microtest wells at spaced locations in said tray for receiving and holding test solutions including lymphocytes and selective cytotoxic reagents capable of lysing selected lymphocytes, said microtest wells including an upper rim on said tray top surface having a surface area sufficient to allow introduction of lymphocytes and reagents into said wells, a bottom having a surface area less than the surface area of said well opening and a well side wall extending at a constant slope downward between said upper rim and said well bottom, wherein the improvement comprises:

an arcuate side wall having a slope which gradually increases from less than vertical near the well rim to substantially vertical at the well bottom to thereby promote localization of said lymphocytes toward said well bottom.

* * * * *